(12) United States Patent
Wiley

(10) Patent No.: US 11,337,467 B2
(45) Date of Patent: May 24, 2022

(54) ARTICLE OF CLOTHING WITH MAGNETS

(71) Applicant: Marta Wiley, Litchfield Park, AZ (US)

(72) Inventor: Marta Wiley, Litchfield Park, AZ (US)

( * ) Notice: Subject to any disclaimer, the term of this patent is extended or adjusted under 35 U.S.C. 154(b) by 360 days.

(21) Appl. No.: 16/654,416

(22) Filed: Oct. 16, 2019

(65) Prior Publication Data

US 2020/0046038 A1    Feb. 13, 2020

Related U.S. Application Data

(63) Continuation of application No. 16/361,606, filed on Mar. 22, 2019, now abandoned.

(60) Provisional application No. 62/652,507, filed on Apr. 4, 2018.

(51) Int. Cl.
| | | |
|---|---|---|
| A41D 1/00 | (2018.01) | |
| A41D 31/04 | (2019.01) | |
| A61N 2/06 | (2006.01) | |
| A61H 39/00 | (2006.01) | |
| A41D 27/00 | (2006.01) | |
| A61N 2/00 | (2006.01) | |

(52) U.S. Cl.
CPC ............ *A41D 1/002* (2013.01); *A41D 27/00* (2013.01); *A41D 31/04* (2019.02); *A61H 39/00* (2013.01); *A61N 2/008* (2013.01); *A61N 2/06* (2013.01); *A41D 2400/32* (2013.01); *A61H 2201/10* (2013.01)

(58) Field of Classification Search
CPC .......... A61N 2/00–12; A41D 2400/324; A41D 1/002; A41D 27/00; A41D 31/04; A61H 2201/10; A61H 2201/165; A61H 39/00
See application file for complete search history.

(56) References Cited

U.S. PATENT DOCUMENTS

| | | |
|---|---|---|
| 4,735,572 A | 4/1988 | Clifford |
| 5,950,239 A | 9/1999 | Lopez |
| 6,763,525 B1 | 7/2004 | Spector |
| 7,309,236 B1 | 12/2007 | Ward |
| 2006/0122544 A1 | 6/2006 | Ciluffo |
| 2008/0233549 A1 | 9/2008 | Daniels |

(Continued)

FOREIGN PATENT DOCUMENTS

CN    108634402 A  * 10/2018

OTHER PUBLICATIONS

Translation of CN108634402A (Year: 2018).*

(Continued)

*Primary Examiner* — Thaddeus B Cox
(74) *Attorney, Agent, or Firm* — Boudwin Intellectual Property; Daniel Boudwin

(57) ABSTRACT

An article of clothing with magnets. The article of clothing with magnets is at least one material configured to receive a body part of a user, as well as at least one magnet disposed on the material. In various embodiments, the at least one magnet can be comprised of magnetic discs or magnetic strips. The article of clothing can cover the entire body, or various parts of an individual's body. In another embodiment, the at least one magnet is disposed on the inner layer such that it is in contact with a wearer's skin. In various embodiments, the at least one magnet is disposed at a plurality of meridian lines, a plurality of pressure points, a plurality of muscle groupings, a plurality of acupuncture points, or combinations thereof.

15 Claims, 4 Drawing Sheets

(56) References Cited

U.S. PATENT DOCUMENTS

| | | |
|---|---|---|
| 2008/0282437 A1 | 11/2008 | Park |
| 2012/0129418 A1 | 5/2012 | Ingle |
| 2013/0310627 A1 | 11/2013 | Fanco et al. |
| 2014/0038149 A1 | 2/2014 | Cruz |
| 2014/0088338 A1 | 3/2014 | Chang |
| 2015/0273232 A1 | 10/2015 | Fernandez |
| 2017/0181927 A1 | 6/2017 | Lou |

OTHER PUBLICATIONS

Mantash et al., "Dual-band Textile Hexagonal Artificial Magnetic Conductor for WiFi Wearable Applications," 6th EUCAP, 2012, p. 1395-1398 (Year: 2012).*

Marta Wiley Bio-Electromagnetic Supersuit: Unlocking The Hidden Potential Of Magnetic Hydrogen [Kindle Edition] Publication Date: Sep. 9, 2018 https://www.amazon.com/DP/B07H7THDR5.

* cited by examiner

ARTICLE OF CLOTHING WITH MAGNETS

CROSS REFERENCE TO RELATED APPLICATIONS

This application is a continuation application of U.S. patent application Ser. No. 16/361,606 filed on Mar. 22, 2019, now abandoned, which claims the benefit of U.S. Provisional Application No. 62/652,507 filed on Apr. 4, 2018. The above identified patent application is herein incorporated by reference in its entirety to provide continuity of disclosure. Herein incorporated by reference in its entirety to provide continuity of disclosure is the book written by Wiley, M. (Sep. 9, 2018) Bio-Electromagnetic Suit: Unlocking the Hidden Potential of Magnetic Hydrogen [Kindle Edition]. Retrieved from Amazon.com.

BACKGROUND OF THE INVENTION

The present invention relates to alternative medical therapeutic devices. More particularly, the present invention provides for, at least, an article of clothing with at least one magnet disposed on the article of clothing.

Many top athletes utilize an assortment of alternative medical treatments to ensure that their body operates at superhero-like levels. One such alternative medical treatment is magnetic field therapy which manipulates the naturally occurring magnetic field throughout and surrounding the human body. A second such treatment is electromagnetic therapy in which various electrical devices are utilized to deliver low-voltage electricity, magnetic fields, radio waves or other types of electromagnetic waves to an individual. A third such alternative medical treatment is acupuncture which manipulates the naturally occurring flow of energy in the body, sometimes referred to as Qi, through insertion of thin needles into the skin. Through a combination of these alternative medical treatments, individuals seek to not only heal ailments and bring their bodies back into harmony, but also to enhance and extend the quality and length of their lives.

The human body naturally creates electric energy and magnetic fields by various chemical processes, including the transduction of signals in cells such as the heart, brain and peripheral nervous system. Through utilization of such chemical processes, living beings maintain their organs and tissues in an energetic equilibrium. For example, millions of nerve impulses travel through the human brain and throughout the nervous system. Each nerve impulse can be expressed as a wave of electrical activity that passes from one end of a nerve cell to another. As electrochemical energy passes through a human body's cells in such a way an electro-magnetic field is generated. The electro-magnetic field not only affects the cells and the human body as a whole, but such energy can also affect the individual's surroundings. When the body's natural electric flow and magnetic fields are hampered, such as through competing magnetic fields emanating from outside the body, the body's natural systems can become imbalanced.

Magnetic field therapy utilizes external magnets to alter the magnetic fields on an individual's body. Some people utilize magnetic field therapy for treating pain and various illnesses. Magnetic field therapy can be utilized by applying the magnetic field of permanent magnets to a part of a body. Through application of a magnet to specified areas of the body, the natural flow of the body's electricity can be altered and brought back into balance. A similar practice, known as electromagnetic therapy, utilizes magnetic fields generated by electrical devices. Pulsed Electromagnetic Field therapy utilizes bursts of low-level electromagnetic radiation to penetrate the skin down to tissues and bone.

Acupuncture is primarily used for pain relief, but many people have also utilized such treatment for a variety of ailments. In the most common method of acupuncture long thin needles penetrate the skin. Another method, known as electroacupuncture, further utilizes electrical stimulation of the acupuncture needles when they are embedded in the skin. According to traditional practice, a series of meridian lines, representing the flow of energy in an individual's body, can be identified. Acupuncture points can further be identified as points where insertion of the acupuncture needle, as well as stimulation thereof, can provide a therapeutic benefit. For example, manipulation of an acupuncture needle in an acupuncture point can release certain chemicals or substances in the body which can adjust the function of a targeted organ or restore homeostasis.

Devices have been disclosed in the known art that relate to alternative medical therapeutic devices. These include devices that have been patented and disclosed in patent application publications. However, the devices in the known art have several drawbacks. Some people have a fear of needles, and therefor are averse to needle therapy in the form of acupuncture. Acupuncture and magnetic field therapy also rely on the individual remaining stationary such that the needles and/or magnets are properly aligned and stay in place. Therefore, an individual is not able to undergo such therapy without remaining completely still Electromagnetic therapy relies on electrical devices, some of which can be quite large and bulky, and therefor such therapy is not easily transported and cannot be worn by an individual undergoing treatment.

The present invention substantially diverges from the known art and consequently it is clear that there is a need in the art for an improvement to existing alternative medical therapeutic devices. In this regard the present invention substantially fulfills these needs. Accordingly, a device that provides a portable and wearable therapy device capable of providing the benefits of magnetic field therapy, electromagnetic therapy and acupuncture therapy while enabling an individual to continue to move about, and even undergo strenuous exercise, is desired.

SUMMARY OF THE INVENTION

In view of the foregoing disadvantages inherent in the known types of alternative medical therapeutic devices now present in the prior art, the present invention provides an article of clothing wherein the same can be utilized by the user to undergo a magnetic field therapy session, unobtrusively, while moving around or undergoing strenuous exercise. The present article of clothing comprises at least one magnet disposed on the clothing.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
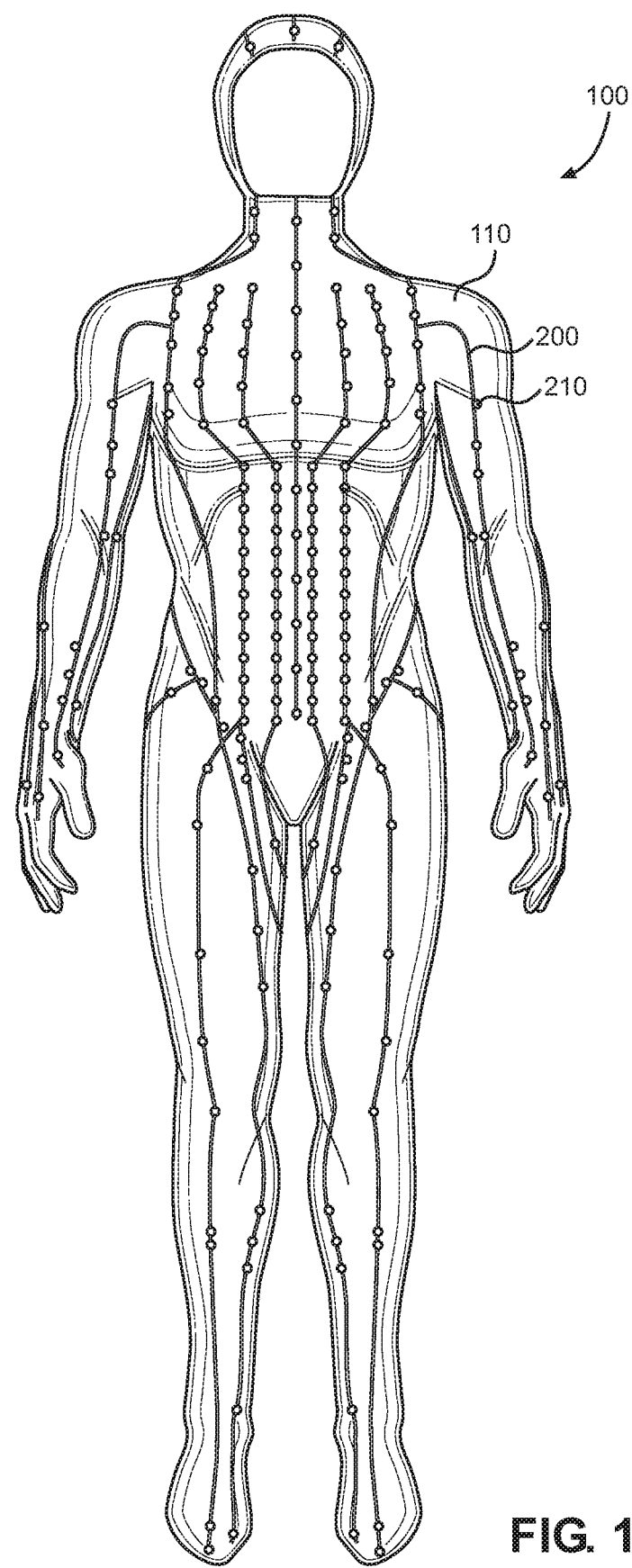
FIG. 1 shows a frontal view of an embodiment of the article of clothing with magnets.

Reference is made herein to the attached drawings. Like reference numerals are used throughout the drawings to depict like or similar elements of the article of clothing with magnets. For the purposes of presenting a brief and clear description of the present invention, a preferred embodiment will be discussed as used for the article of clothing with magnets. The figures are intended for representative purposes only and should not be considered to be limiting in any respect.

Referring now to FIG. 1, there is shown a frontal view of an embodiment of the article of clothing with magnets. The article of clothing with magnets 100 comprises at least one material 110 configured to receive a body part of a user. It should be understood by one of ordinary skill of the art that the at least one material 110 is comprised of any textile suitable to be worn by an individual such as cotton, lycra, nanomaterials, or synthetic blends of fibers. In various embodiments, the at least one material 110 is flexible or has elastic properties such that the material will better fit to the body of a user. It is contemplated by this disclosure that in further embodiments, the article of clothing with magnets further comprises elastic, buttons, snaps, fasteners, zippers, and hook and loop fasteners which secure materials in an article of clothing. In one embodiment the article of clothing with magnets 100 can be configured to be worn by a human. In a further embodiment, the article of clothing with magnets 100 is unisex and configured to be worn by a human of any gender. In another embodiment, the article of clothing with magnets 100 is configured to be worn by an animal, such as a pet.

In one embodiment, the at least one material 110 is configured to withstand large amounts of electromagnetic energy. In another embodiment, the at least one material 110 is an electroactive fabric. In a further embodiment, the electroactive fabric is comprised of electroactive polymers. An electroactive polymer is a polymer that changes its size and shape when stimulated by an electric field. In one embodiment, the article of clothing with magnets 100 comprises a power source electrically connected to at least one magnet disposed on the at least one material 110. In such an embodiment, an electroactive fabric is configured to change its size and shape when such power source is active. In another embodiment, the at least one material comprises memory retaining materials such as shape memory alloys, passive-elastic materials and electrospun fibers.

In one embodiment, the at least one material 110 is a silver-coated nylon fabric. In such an embodiment, cleaning and debridement of the article of the article of clothing with magnets 100 is possible as a silver ion fabric, like silver-coated nylon, is pliable and cleanable with water and soap. Inclusion of silver into the at least one material 110 also provides a restorative benefit when used to treat a wound. Electrically-generated silver ions can penetrate into a wound to create a silver-collagen complex that supports regeneration. Wounds, when treated with specific voltages of electrically generated silver ions, can activate embryonic cells.

In various embodiments, the article of clothing with magnets 100 takes the form of a variety of different articles of clothing. In the shown embodiment, the article of clothing with magnets 100 is of the form of a full body suit that covers an individual's entire body except for their face. It is contemplated by this disclosure that the article of clothing with magnets 100 includes numerous articles of clothing such as:

clothing that covers up to the full body of a user;

clothing that covers a portion of or the full torso of a user, such as a coat, shirt, and a vest;

clothing that covers a portion of or the full legs of a user, such a pants, legging and shorts;

clothing that covers a portion of or the full knees of a user;

clothing that covers a portion of or the full feet of a user, such as socks, shoes, inserts, and sandals;

clothing that covers a portion of or the full arms of a user;

clothing that covers a portion of or the full hands of a user, such as gloves;

clothing that covers a portion of or the full wrist of a user;

clothing that covers a portion of or the full neck of a user;

clothing that covers a portion of or the full head of a user, such as a helmet, hat, headband or ear muffs;

clothing that covers a portion of or the full face of a user, such as a mask;

clothing that covers a portion of or the full midsection of a user, such as underwear, lingerie and a bathing suit;

jewelry, such as earrings, glasses, watches, and bindi.

Figure 2:
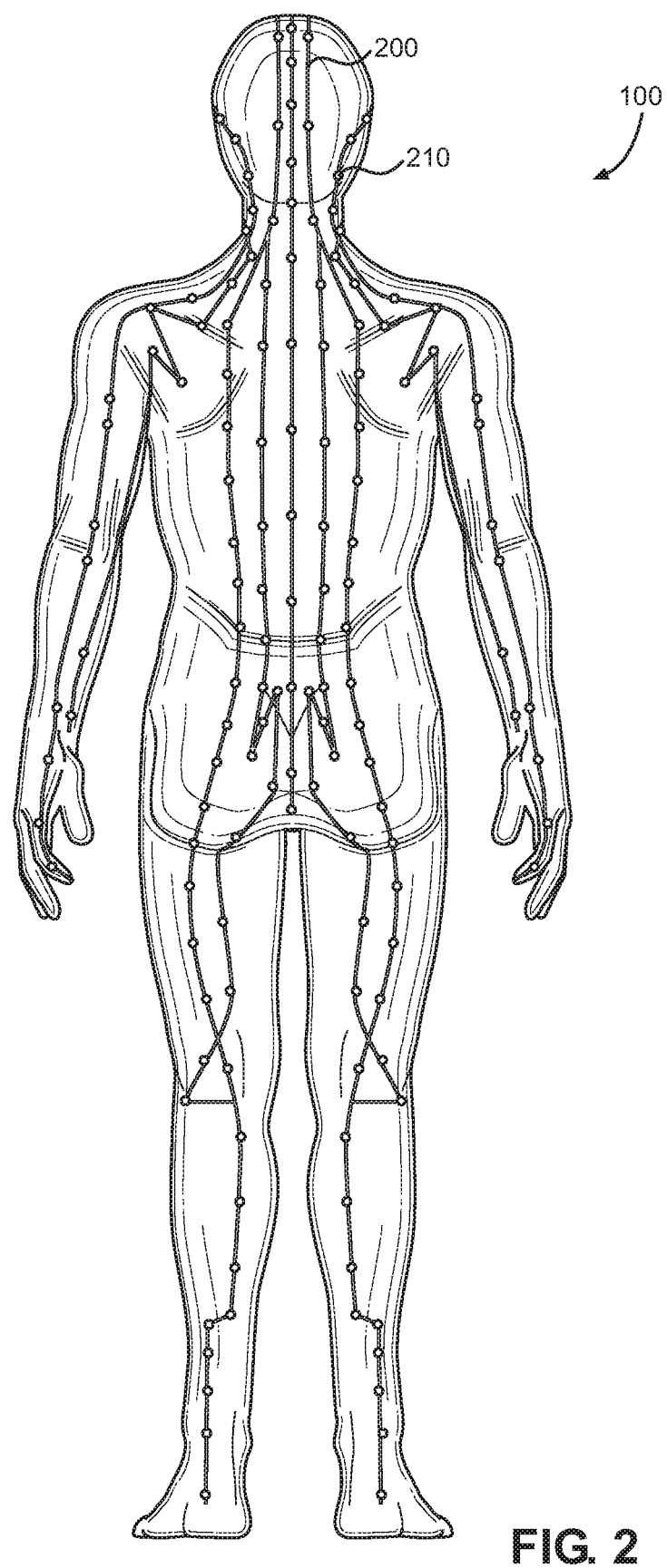
FIG. 2 shows a back view of an embodiment of the article of clothing with magnets.

Referring now to FIG. 2, there is shown a back view of an embodiment of the article of clothing with magnets. In multiple embodiments, indicia are displayed on the external surface of the article of clothing with magnets. In various embodiments, the indicia correspond to a location selected from a group of locations consisting of: a plurality of meridian lines, a plurality of pressure points, a plurality of muscle groupings, a plurality of acupuncture points, and a combination thereof. In other embodiments, other types of indicia, such as a logo, can be displayed on the external surface of the article of clothing with magnets.

In one embodiment, meridian lines 200 are displayed on an external surface of the article of clothing with magnets. In the illustrated embodiment, the meridian lines 200 correspond to the meridian lines associated with the flow of an individual's body's energy. Meridian lines 200 can be mapped by one of ordinary skill in the art, and such mapping can be displayed on an exterior surface of the article of clothing with magnets. Therefore, it should be understood that one of ordinary skill in the art is able to determine the placement of the meridian lines 200 on the corresponding part of the article of clothing with magnets.

In another embodiment, acupuncture points 210 are displayed on an exterior surface of the article of clothing with magnets. Acupuncture points 210 are those points on an individual's body used in acupuncture therapy. Traditionally, acupuncture points 210 on the body at those areas of the body thought to have a specific energetic function. Some acupuncture points are located at the meeting of meridian pathways while others are junctions with an internal pathway of the meridian. Some acupuncture points can move energy inward towards the interior of the body, while other acupuncture points can bring energy to the surface. Traditionally the human body has 365 acupuncture points and 14 meridian pathways. Each meridian pathway can act as a passageway that delivers energy from the acupuncture points to various systems of the body. Acupuncture points 210 can be mapped by one of ordinary skill in the art, and such mapping can be displayed on an exterior surface of the article of clothing with magnets. Therefore, it should be understood that one of ordinary skill in the art is able to determine the placement of the acupuncture points 210 on the corresponding part of the article of clothing with magnets.

In other embodiments, pressure points and muscle groupings are displayed on an exterior surface of the article of clothing with magnets. Pressure points, muscle groupings, and other such anatomical information are well known in the art, and therefore it should be understood that one of ordinary skill in the art is able to determine the placement of such information on the corresponding part of the article of clothing with magnets. Pressure points, muscle groupings, and other such anatomical information can be mapped by one of ordinary skill in the art, and such mapping can be displayed on an exterior surface of the article of clothing with magnets.

The indicia displayed on the exterior surface of the article of clothing with magnets can aid an individual user in determining the proper size and shape of the article of clothing with magnets. By aligning the indicia displayed with known landmarks on an individual user's body, the user is able to properly choose and fit an appropriate size and shape of an article of clothing with magnets to their unique body size and shape.

Figure 3:
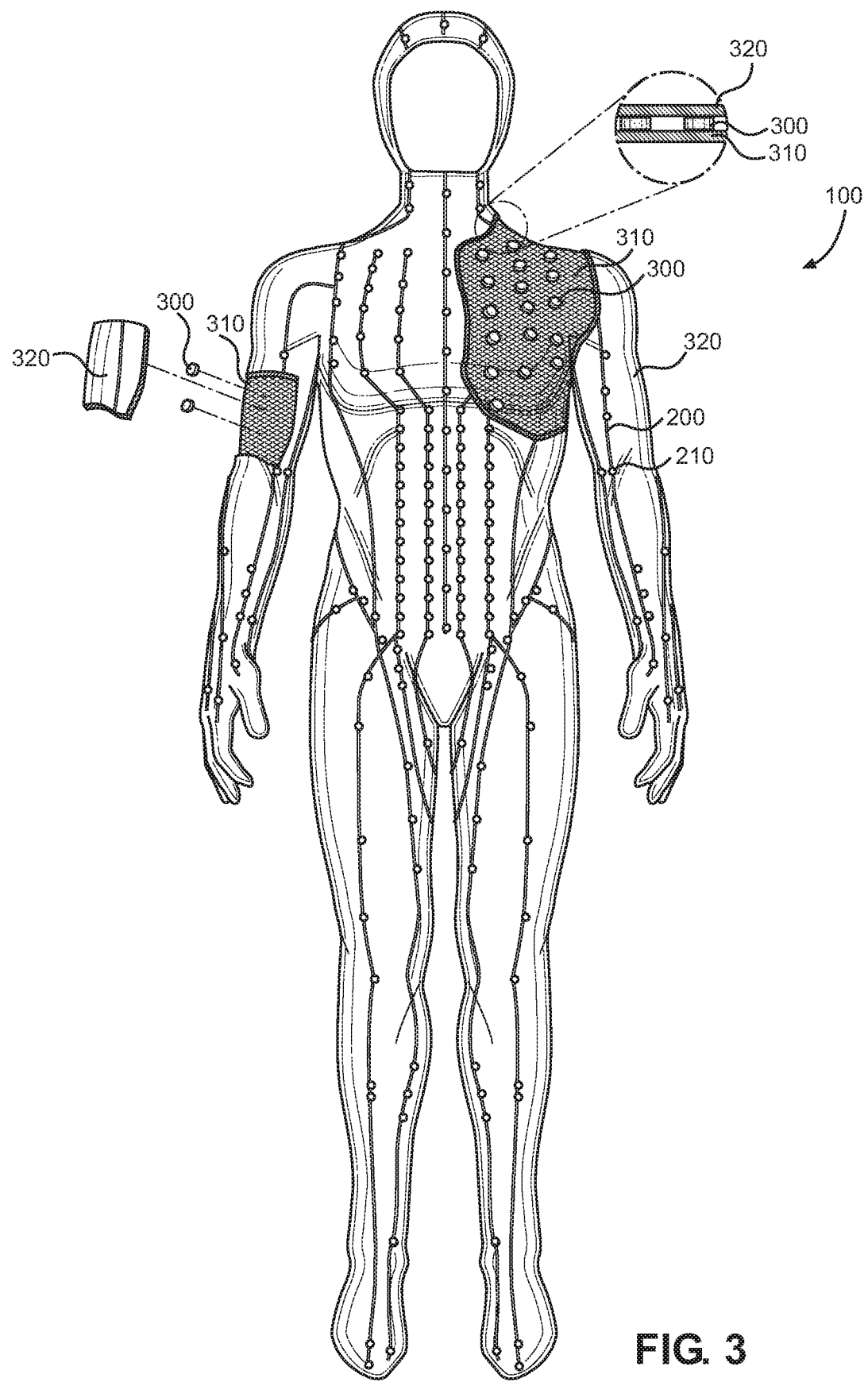
FIG. 3 shows a transparent frontal view of an embodiment of the article of clothing with magnets.

Referring now to FIG. 3, there is shown a transparent frontal view of an embodiment of the article of clothing with magnets. The at least one material 110 is comprised of a single, or multiple layers of the at least one material 110. In another embodiment, the at least one material 110 is combined with other, different materials. In such a manner, the at least one material 110 can be combined with other materials to provide a more comfortable, form-fitting, or aesthetically appealing article of clothing.

At least one magnet 300 is disposed on the at least one material 110. In the shown embodiment, the at least one magnet 300 is disposed between a first layer 310 and a second layer 320 of the at least one material 110. In another embodiment, the at least one magnet 300 is disposed on the inner surface of a single layer of the at least one material, the inner surface being that surface of the at least one material that rests against the body of an individual user. In such an embodiment, the distance between the at least one magnet 300 and the body of the individual user is minimized for greater surface coverage of the magnet on the individual user's body. In another embodiment, the at least one magnet 300 is disposed on an outer surface of a single layer of the at least one material, being that surface of the at least one material 110 that is furthest from an individual user's body. In such an embodiment, the at least one material 110 can rest against the individual user's body for a more comfortable fit. A further advantage of such placement is to reduce the friction that can be caused by the body rubbing against the body as can occur when the at least one magnet 300 is disposed on the inner layer.

In various embodiments, each of the at least one magnet 300 can be a variety of shapes including, but not limited to, strips, discs and hexagons. In further embodiments, the article of clothing with magnets can comprise a combination of differently shaped magnets. By utilizing such a variety of magnets, the article of clothing with magnets can be precisely disposed on desired areas of the at least one material 110.

In various embodiments, the at least one magnet 300 is disposed at a location selected from a group of locations consisting of: a plurality of meridian lines 200, a plurality of pressure points, a plurality of muscle groupings, a plurality of acupuncture points 210, and a combination thereof. In further embodiments, multiple magnets are placed on a multitude of such points and landmarks. In this manner, an article of clothing can have a magnet placed at each location corresponding to each part of a meridian line, pressure point, muscle grouping, acupuncture point, or other anatomical landmark. It is contemplated by this disclosure that the article of clothing with magnets can include up to as many magnets, of a variety of shapes and sizes, as are necessary to cover such landmarks.

Figure 4:
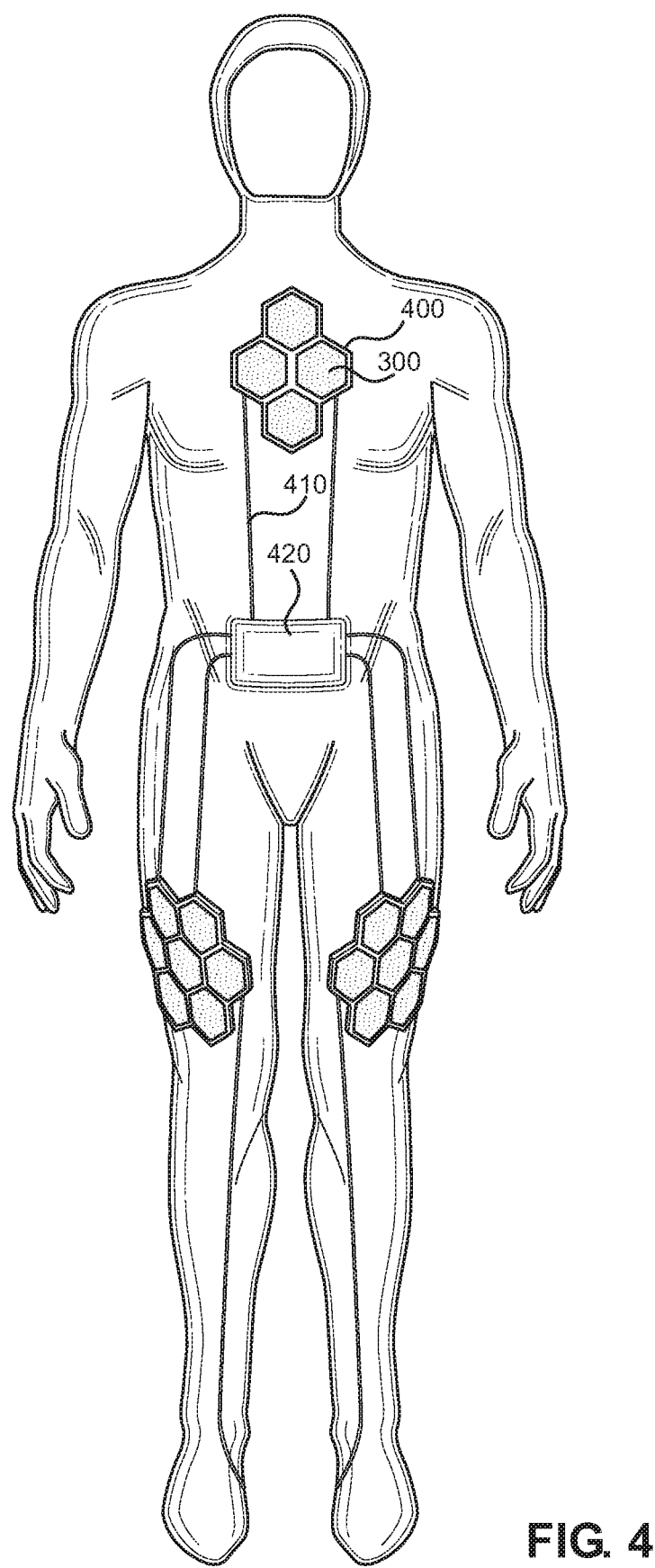
FIG. 4 shows a transparent frontal view of an embodiment of the article of clothing with magnets.

Referring now to FIG. 4, there is shown a transparent frontal view of an embodiment of the article of clothing with magnets. In the shown embodiment, the at least one magnets 300 are in the shape of a hexagon. Hexagonal geometry is tied into complex mathematical concepts such as vortex mathematics, Fibonacci sequences, and the Golden Spiral and is essential when utilized in combination with acupuncture points. Electromagnetic currents run positive on the right side of the body and negative on the left side of the body. Thus, each acupuncture point is positively and negatively charged in nature. Reversing the currents from the body's natural yin and yang so that the currents cross at the chakras results in an inducement of positive charge on the left side of the body and negative charge on the right side of the body which produces regenerative effects in the body.

The hexagonal geometry enables a specific frequency of 432 hertz to be utilized as such a frequency is integral to the hexagonal geometry. The hexagonal geometry, when activated by the acupuncture points, and specifically by the 432 hertz frequency, creates a field around the body. In the shown embodiment, 432 hertz frequencies are employed and are driven by the hexagonal shape of the magnets. In other embodiments, frequencies along the Fibonacci sequence are utilized for their cross-current regeneration characteristics. The 432 hertz frequency move Chi through the body, creating a toroidal field. The present invention employs hexagonal shaped magnets that cater to the spin state of the toroidal field that cannot be activated by traditional magnets alone. In the shown embodiment, the at least one magnets 300 are arranged in a tile configuration around a targeted grouping of acupuncture points. In this manner, the hexagonal geometry of the at least one magnets 300 can be utilized at specific targeted acupuncture points. By tiling the hexagonal magnets 300, the entire surface of the article of clothing can be encapsulated by the hexagonal magnets 300, without any gaps between the magnets. In one embodiment, at least one vertex of each hexagonally tiled magnet 300 is in contact with an acupuncture point. In another embodiment, at least one edge of each hexagonally tiled magnet 300 is in contact with an acupuncture point.

In various embodiments, each of the at least one magnet 300 can be a variety of shapes including, but not limited to, strips, discs and hexagons. In one embodiment electrodes 400 can be in electrical communication 410 with the at least one magnets 300. In such an embodiment, the electrodes 400 surround the at least one magnets 300 and are configured to remain in contact with a user's skin. In a further embodiment, the electrodes are comprised of gold, silver, or a combination thereof. In the shown embodiment, each of the at least one magnets 300 is in electrical communication 410 with a controller 420. The controller 420 is electrically connected to a power source. The controller 420 can pass electrical current from the power source to each of the at least one magnets 300. In one embodiment the controller 420 can selectively pass current to a selection of the at least one magnets 300. In another embodiment, the controller 420 passes a selective amount of current to the at least one magnet 300. In a further embodiment, the controller 420 passes a selective amount of current to a selection of the at least one magnet 300. In such a manner, a user can determine how much current to be passed to each individual magnet 300.

In one embodiment, the controller 420 is operably connected to a transceiver and wirelessly connected to a remote controller. In a further embodiment, the remote controller is programmed with a plurality of predetermined patterns and levels of current to be passed to the at least one magnets 300. In another embodiment, a user can program the remote controller to pass a selective level of current to a selection of the at least one magnets 300. In such a way, a user can pass current to a grouping of magnets in order to target an area of the user's body that the user desires to undergo a therapy session.

In one embodiment, the power source is a rechargeable battery. In another embodiment, the powersource is a selectively removable battery. In another embodiment, the power source is at least one button that is electrically connected to a solar panel and a rechargeable battery. In such an embodiment, the user can recharge the battery power source by exposure to light.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An article of clothing, comprising:
   at least one flexible material configured to receive a body part of a user;
   the at least one flexible material comprising at least one layer;
   the at least one layer having an inner surface configured to rest flush against the body part of the user;
   a plurality of hexagonally tiled magnets disposed on the at least one flexible material.

2. The article of clothing of claim 1, wherein the at least one flexible material is silver-coated nylon fabric.

3. The article of clothing of claim 1, wherein the at least one flexible material is electroactive fabric.

4. The article of clothing of claim 1, wherein the at least one flexible material has elastic properties.

5. The article of clothing of claim 1, wherein the outer surface comprises indicia corresponding to a location selected from a group of locations consisting of: a plurality of meridian lines, a plurality of pressure points, a plurality of muscle groupings, a plurality of acupuncture points, and a combination thereof.

6. The article of clothing of claim 1, wherein at least one vertex of each hexagonally tiled magnet is configured to be in contact with an acupuncture point.

7. The article of clothing of claim 1, wherein at least one edge of each hexagonally tiled magnet is configured to be in contact with an acupuncture point.

8. An article of clothing, comprising:
   at least one flexible material configured to receive a body part of a user;
   the at least one flexible material comprising at least one layer;
   the at least one layer having an inner surface configured to rest flush against the body part of a user;
   a plurality of hexagonally tiled magnets disposed on the at least one flexible material;
   the plurality of hexagonally tiled magnets electrically connected to a power source;
   the power source operably connected to a controller.

9. The article of clothing of claim 8, wherein the at least one flexible material further comprises solar powered buttons.

10. The article of clothing of claim 8, wherein the at least one flexible material is silver-coated nylon fabric.

11. The article of clothing of claim 8, wherein the at least one flexible material is electroactive fabric.

12. The article of clothing of claim 8, wherein the at least one flexible material has elastic properties.

13. The article of clothing of claim 8, wherein the outer surface comprises indicia corresponding to a location selected from a group of locations consisting of: a plurality of meridian lines, a plurality of pressure points, a plurality of muscle groupings, a plurality of acupuncture points, and a combination thereof.

14. The article of clothing of claim 8, wherein at least one vertex of each hexagonally tiled magnet is configured to be in contact with an acupuncture point.

15. The article of clothing of claim 8, wherein at least one edge of each hexagonally tiled magnet is configured to be in contact with an acupuncture point.

\* \* \* \* \*